US010379110B2

(12) United States Patent
Elfverson et al.

(10) Patent No.: US 10,379,110 B2
(45) Date of Patent: Aug. 13, 2019

(54) CALIBRATION REAGENT AND METHOD (75) Inventors: Göran Elfverson, Bälinge (SE); Per Matsson, Knivsta (SE); Mats Nystrand, Uppsala (SE)

(73) Assignee: PHADIA AB, Uppsala (SE)

(*) Notice: Subject to any disclaimer, the term of this patent is extended or adjusted under 35 U.S.C. 154(b) by 0 days.

(21) Appl. No.: 14/344,894

(22) PCT Filed: Sep. 14, 2012

(86) PCT No.: PCT/SE2012/050977
§ 371 (c)(1),
(2), (4) Date: Mar. 26, 2014

(87) PCT Pub. No.: WO2013/039450
PCT Pub. Date: Mar. 21, 2013

(65) Prior Publication Data
US 2014/0228244 A1    Aug. 14, 2014

Related U.S. Application Data (60) Provisional application No. 61/534,578, filed on Sep. 14, 2011.

(30) Foreign Application Priority Data

Sep. 14, 2011 (SE) ...................................... 1150834

(51) Int. Cl.
*G01N 33/53* (2006.01)
*G01N 33/68* (2006.01)
*G01N 33/96* (2006.01)
*C07K 16/00* (2006.01)

(52) U.S. Cl.
CPC ......... *G01N 33/5302* (2013.01); *C07K 16/00* (2013.01); *G01N 33/6854* (2013.01); *G01N 33/96* (2013.01)

(58) Field of Classification Search
CPC ........... G01N 33/5302; G01N 33/6854; G01N 33/96; C07K 16/00
See application file for complete search history.

(56) References Cited

U.S. PATENT DOCUMENTS

| 6,015,662 A | 1/2000 | Hackett et al. |
| 6,916,666 B1 * | 7/2005 | Mendel-Hartvig et al. .. 436/518 |
| 2005/0048468 A1 | 3/2005 | Chen et al. |
| 2008/0220980 A1 * | 9/2008 | Lea .................. G01N 33/52 506/9 |
| 2009/0269780 A1 * | 10/2009 | Sorensen ............ G01N 33/543 435/7.1 |
| 2009/0286240 A1 * | 11/2009 | Guyon .............................. 435/6 |
| 2010/0049444 A1 * | 2/2010 | Likuski ............ G01N 33/723 702/19 |
| 2010/0150860 A1 | 6/2010 | Fan et al. |
| 2011/0306511 A1 | 12/2011 | Lea |

FOREIGN PATENT DOCUMENTS

| CN | 101526535 A | 9/2009 |
| CN | 102066899 A | 5/2011 |
| CN | 102388306 A | 3/2012 |
| JP | 2000-505543 A | 5/2000 |
| RU | 2426745 C2 | 8/2011 |
| WO | 97/27486 A1 | 7/1997 |
| WO | 02/29415 A1 | 4/2002 |
| WO | 2005/021036 A1 | 3/2005 |
| WO | 2011/050463 A1 | 5/2011 |

OTHER PUBLICATIONS

Official Action dated Feb. 28, 2015 from corresponding Chinese Application No. 201280044625.7, and English Translation.
Achim Knappik et al, Annals of the New York Academy of Sciences, 1173:190-198 (2009).
Bohman et al, Allergy, 62(83):49 (2007).
Rodriguez-Mozaz et al, Biosensors and Bioelectronics, 19(7):633-640 (2004).
Suzuki et al, Exp. Anim., 60(2):193-196 (Apr. 2011).
International Type Search Report from Swedish Priority Application 1150834-8 dated Feb. 27, 2012.
IPRP dated Dec. 19, 2013.
Hutchinson, Kathleen, Hybritech free Prostate Specific Antigen (free PSA) on the Beckman Access, University of Washington Medical Center, 2001-2002.
Bio-Rad BioPlex 2200, 510(k) No. K041658, Substantial Equivalence Determination Decision Summary (2004).
Forkman, Johannes, "Optimal Calibration in Immunoassay and Inference on the Coefficient of Variation," Doctoral Thesis, Swedish University of Agricultural Sciences, Uppsala, Sweden (2008).
Hamilton, Robert G., "Assessment of human allergic diseases," Clinical Immunology: Principals and Practice, 3rd Edition, Rich et al, Editors, London: Mosby, Elsevier Ltd. 2008:1471-1474.
Harwanegg et al, "Protein microarrays for the diagnosis of allergic diseases: state-of-the-art and future development," Clin Chem Lab Med, 43(12):1321-1326 (2005).
Matsson et al, "Analytical Performance Characteristics and Clinical Utility of Immunological Assays for Human Immunoglobulin E (IgE) Antibodies and Defined Allergen Specificities: Approve Guideline—Second Edition," Clincial and Laboratory Standards Institute, 29(9) 1-145, (2009).
Wood et al, "Accuracy of IgE antibody laboratory results," Annals of Allergy, Asthma & Immunology, 99:34-41 (Jul. 2007).
Official Action dated Sep. 21, 2015 from corresponding Chinese Application No. 201280044625.7, and English Translation.

(Continued)

*Primary Examiner* — Andrea S Grossman
(74) *Attorney, Agent, or Firm* — Porter Wright Morris & Arthur LLP (57) ABSTRACT

The present invention relates to a method for calibrating a multiplex assay, comprising: adding a calibration reagent to a solid phase on which a plurality of capturing agents are immobilized, adding a detection molecule which has a capacity to bind to the calibration reagent, detecting bound detection molecule, thereby creating a calibration curve, wherein the calibration reagent comprises at least two different binding molecules, wherein each binding molecule has a capacity to bind specifically to a capturing agent immobilized on the solid phase and a capacity to bind to a detection molecule. Further provided is a multiplex assay system comprising such a calibration reagent.

24 Claims, 7 Drawing Sheets

(56) References Cited

OTHER PUBLICATIONS

Official Action from corresponding Japanese Application No. 2014-530631, dated Jul. 20, 2016.
English Translation of Official Action from corresponding Russian Application No. 2014114539, dated Sep. 14, 2012.
English Translation of Decision on Grant dated May 2, 2017 from corresponding Russian Application No. 2014114539.
Official Action dated Jun. 2, 2017 from corresponding CN 201610316424.8 and English translation of Official Action.
Official Action dated Dec. 20, 2018 from corresponding Korean Application No. 10-2014-7009368, and English Translation.
Examination Report dated Jul. 27, 2018 from corresponding Indian Application No. 1402/DELNP/2014.
Official Office Action dated Nov. 6, 2018 from corresponding Canadian Application No. 2,845,807.

* cited by examiner

CALIBRATION REAGENT AND METHOD

FIELD OF THE INVENTION

The present invention relates to the field of multiplex assays, and more specifically to a multiplex assay system, a method for calibrating multiplex assays and a calibration reagent.

BACKGROUND OF THE INVENTION

In singleplex assays an analyte is the chemical component measured in an analytical procedure. In immunoassay, the analyte is either an antibody or an antigen. Antibodies are proteins in the blood that are produced by the immune system for protection against foreign bodies, while the foreign bodies are the antigens. The antibodies bind to the antigens. The antigens or the antibodies are labelled before analysis, in order to give a measurable signal. This label can be an enzyme, a radioactive isotope, or fluorescein. The signals obtained from an immunoassay can be radioactivity or emission of light. These signals are commonly called responses. The immunoassay involves chemical reactions between clinical samples obtained from patients and reagents (i.e. chemical solutions) performed under standardised conditions. The result is a response that is related to the concentration of the analyte in the sample. In competitive immunoassay, the analyte is unlabelled and competes with labelled molecules. The response is then a decreasing function of the analyte concentration. In non-competitive immunoassay the labelled molecules bind to the analyte, and the response is an increasing function. In either case, the exact relationship between response and concentration needs to be estimated. This estimation is called calibration. For calibration, samples with known concentrations are required. These specific samples are called calibrators or standards, and are usually prepared in advance. For example, a single sample with a known high concentration can be dissolved in water or animal serum to produce calibrators with a few specified lower concentrations covering the range of measurement. When discussing statistical design for calibration, the specified calibrator concentrations are called design points. Because the calibrators are specially prepared, but the samples are not, the calibrators and the clinical samples may react in slightly differently ways. Usually, a set of clinical samples with unknown concentrations is assayed together with the calibrators in an assay run. A calibration curve is fitted to the responses of the calibrators. This curve can be a straight line or some other monotonic function. The responses of the clinical samples are transformed into estimates of concentration through the fitted calibration curve. This method for estimation of sample concentrations is called inverse prediction.

Because the relationship between response and concentration may change from one assay run to another, calibrators are often included in each assay run, so that each can be calibrated separately. However, in some systems it is assumed that the relationship is stable, so that calibration needs to be performed less often, for example only once a month or when new batches of reagents are taken into use (Forkman J., Doctoral Thesis, Swedish University of Agricultural Sciences, Uppsala, 2008, ISSN 1652-6880, ISBN 978-91-86195-13-7).

Multiplex assays, by which analytes of multiple specificities are detected in a single sample specimen using a single reaction mixture of reagents, are known in the art. An important component of these assays is the calibration system used to define the level of reagent i.e. antibody or biomarker that is measured by the assay. Classically, these levels were reported using a number of arbitrary units, depending on the degree of quantitation afforded by the assay system. In qualitative assays, the targeted molecule in the serum specimen is reported as positive or negative based on the level of the response signal measured, as compared with a pre assigned positive threshold level. In a number of semi quantitative assays, both a positive/negative result, the magnitude of the signal measured (eg, luminescent units [LU], millivolts [mVolts]), the class score, the adjusted or normalized counts (from modified scoring systems), or the percent of the lowest control (alternative scoring system) are reported. The magnitude of the signal is related in terms of rank order to (but not consistently directly proportional to) the quantity of the molecule present in the test serum.

We will here exemplify with three different test types of multiplex assays known in the art:
1) Analysis of specific IgE;
2) Analysis of specific IgG; and
3) Analysis of non-immunoglobulin biomarkers (antigens).

Common analysis methods for specific immunoglobulins are 1) specific IgE analysis for the purpose of detecting allergy/hypersensitivity, and 2) specific IgG analysis for the purpose of detecting for example autoimmune diseases or infectious diseases. Disease relevant antigens are deposited onto a micro array at defined locations. These antigens are exposed to a patient sample including immunoglobulins that may bind to a selected antigen. The specific immunoglobulin is detected with an immunoglobulin specific reagent (reporter molecule) that interacts with the specific immunoglobulin, and that interaction can be analysed through the detection system. It is thereby possible to detect all different immunoglobulins specific for a certain antigen. For test type 3), analysis of non-immunoglobulin biomarkers (antigens), such as prostate cancer biomarkers in serum, molecules that have a capability to bind to the biomarkers of interest are deposited onto a micro array at defined locations. The deposited molecules may for example be biomarker-specific antibodies, enzymes or other molecules that are complementary to the biomarkers of interest. The deposited molecules are exposed to a patient sample including biomarkers that may bind to a selected deposited molecule. The specific biomarker is detected with a biomarker specific reagent (reporter molecule) that interacts with the specific biomarker, and that interaction can be analysed through the detection system.

For example, in the field of specific IgE detection, WO2002029415 A1 describes a method for the detection of an allergen-specific immunoglobulin in a sample, and a method for in vitro diagnosis of allergies in an individual. Clinical manifestations such as asthma, hay fever, atopic eczema and gastro intestinal symptoms develop after exposure to specific allergens. Determination of the sensitization pattern to specific and/or cross reactive allergen components assists in a more detailed evaluation of the allergic patient.

Commercially available IgE antibody immunoassays can be classified into a qualitative, semi quantitative, or quantitative assay, depending on the degree to which the assay result accurately reflects the quantity of IgE antibody in the test specimen and the assay's precision requirements. Such immunoassays traditionally measure either the total serum IgE levels or allergen-specific IgE levels.

However, while different technology platforms report their IgE results in seemingly identical classes or units, studies have shown differences between technology platforms in the ability to detect total IgE and specific IgE activity (Wood R A et al, Ann Allergy Asthma Immunol. 2007, 99: 34-41).

Quantitative IgE antibody assays employ the most advanced methods of assay calibration. The purpose of the calibration portion of the quantitative assay is to define the dose-response relationship of the assay so response results obtained by testing patients' sera can be interpolated in dose units that relate to the relative quantity of IgE antibody in the serum. Both homologous and heterologous interpolation methods have been successfully used. The homologous interpolation procedure promotes overall assay parallelism and maximizes the assay's working range by using the same solid-phase allergen throughout the assay, and constructing a calibration curve with human IgE antibody of the same allergen specificity as is to be detected in the test sera. In general, the IgE antibody-containing reference serum pool dilutes out in the same manner as the test serum IgE, thus ensuring assay parallelism. The primary limitation of this approach is the requirement for liter quantities of human serum pools that contain IgE antibody specific for each allergen specificity to be tested. It is difficult to maintain a serum bank that can supply these large quantities of human serum in a reproducible manner between lots, especially for the less common allergen specificities. Because of constraints placed on assays using the homologous interpolation calibration as a result of limited IgE antibody-containing human serum pools, heterologous interpolation from a total IgE calibration curve has been adopted as the calibration strategy for present day quantitative IgE antibody assays that involve hundreds of different allergen specificities. The heterologous interpolation system has become the industry standard. In the heterologous interpolation system, a total serum IgE calibration curve is run simultaneously with the allergen-specific IgE portion of the assay, using an IgE calibrator that is traceable to the WHO 75/502 Standard (I/LA20-A2 Analytical performance characteristics and clinical utility of immunological assays for human immunoglobulin E (IgE) antibodies and defined allergen specificities; Approved Guideline, ISBN no. 1-56238-695-6).

IMMUNOCAP ISAC® is an in vitro diagnostic test using microarray chip technology. It allows simultaneous measurement of specific molecules in a single test, using only a few μl of fluid, e.g. serum or plasma sample. It may be used for analysis of any biomarker, including IgE, IgG and non-immunoglobulin biomarkers.

For example, in the case of analysing specific IgE antibodies by use of IMMUNOCAP ISAC®, a specific IgE (sIgE) chip delivers results for over a hundred components from more than 50 allergen sources. Allergen components that are immobilized on a solid substrate in a microarray format react with the specific IgE in the patient sample. After washing away nonspecific IgE, fluorescence-labeled anti-human IgE antibody is added to form a complex. After incubation, unbound fluorescence labeled anti-human IgE antibodies are removed by washing. The procedure is followed by fluorescence measurement using an appropriate microarray scanner. The higher the response value, the more specific IgE is present in the specimen.

The test results are analyzed with PHADIA® Microarray Image Analysis (MIA) Software and ISAC Standardized Units for specific IgE (ISU-E) are calculated (Protein microarrays for the diagnosis of allergic diseases: state-of-the-art and future development, Clinical Chemical Laboratory Medicine, Volume 43, Issue 12, Pages 1321-1326).

The results are presented semi-quantitatively in four classes (0=Undetectable or Very Low, 1=Low, 2=Moderate to High, 3=Very High). Phadia MIA Software automatically performs this calculation.

Calibration of an IMMUNOCAP ISAC® microarray chip is made against an in-house reference preparation, or calibration reagent, and measured IgE antibody concentrations are expressed as arbitrary units; ISAC Standardized Units for IgE (ISU-E). The IMMUNOCAP ISAC® in-house reference preparation is calibrated against IMMUNOCAP® Specific IgE (with antibody concentrations expressed as kilo-unit IgE per liter; $kU_A/l$), which is standardised against the WHO reference preparation 75/502 for IgE (Hamilton R G, Assessment of human allergic diseases. In: Clinical Immunology, Principles and Practice, ed. Rich R R, $3^{rd}$ ed, 2008, p. 1471-84; see page 1476).

IMMUNOCAP ISAC® may also be used in a similar way to analyse specific IgG and/or other biomarkers (antigens and antibodies).

The present calibration systems normally include the independent calibration of each antigen towards the corresponding specific antibody. This may be illustrated by Biorad's Bioplex ANA screen, which uses multiplex immunoassay flow, and which detects the presence of clinically relevant circulating autoantibodies in serum or plasma. At the same time, this is an example of the second type of multiplex assays as mentioned above, i.e. the analysis of specific IgG. The Bioplex system uses a bead based multiplex assay format and the calibration process is described as follows: "While the identity of the dyed beads is determined by the fluorescence of the dyes, the amount of antibody captured by the antigen is determined by the fluorescence of the attached PE" (i.e. phycoerythrin; the fluorescent detection molecule). "Raw data is calculated in relative fluorescence intensity (RFI) and fluorescence ratio (FR). Three additional dyed beads, Internal Standard Bead (ISB), Serum Verification Bead (SVB) and a Blank Bead (BB) are present in each reaction mixture to verify detector response, the addition of serum or plasma to the reaction vessel and the absence of significant non-specific binding in serum or plasma. Refer to the BioPlex 2200 System Operation Manual for more information. The instrument is calibrated using a set of six (6) distinct calibrator vials, supplied separately by Bio Rad Laboratories. For dsDNA, six (6) vials, representing six (6) different levels of antibody concentrations, are used for quantitative calibration, and results for patient samples are expressed in IU/mL. Results of sA IU/mL are negative, 5-9 IU/mL are indeterminate, and results of 10 IU/mL or higher are considered positive for dsDNA antibody. For the other twelve (12) beads, four (4) vials representing four (4) different antibody concentrations are used for semi-quantitative calibration. The result for each of these antibodies is expressed as an antibody index (AI). An AI of 1.0 indicates an antibody cut-off concentration that corresponds to approximately the 99th percentile of values obtained from a non-diseased population; results of 1.0 or higher are reported as positive. Results of <1.0 are reported as negative" (Biorad, Bioplex 2200 Ana Screen SIO(k) Summary, FDA 510(k), SIO(k) Number k041658).

The third type of multiplex assays includes the analysis of non-immunoglobulin biomarkers (antigens), e.g. prostate cancer biomarkers. This is an example in which a traditional singleplex immunoassay is converted into a multiplex format. This has been exemplified through several bead based assays as well as limited multiplexing using various solid arrays. In all these assays it is of essence that each individual test is calibrated separately, which tends to become tedious and cumbersome when running multiplex formats.

Beckman Coulter describes the calibration of its Access Hybritech free PSA assay, which is an analysis of the free form of the prostate cancer biomarker PSA, as a set of 5 different standard points and one negative sample totaling 6 different calibration intervals. It is also evident that the free PSA concentrations are dependent on the standard used to calibrate the assay (Beckman Coulter, Inc., 2010, A85087C, Access Hybritech free PSA).

At present, as described above, calibration of immunoassays for the detection of different types of molecules usually necessitates running several calibration samples for each test, including calibration samples of different concentrations and calibration samples containing different calibrator molecules. Consequently, such a calibration technique is time-consuming and may be imprecise due to systematic assay system variability over time.

The object of the present invention is to provide a reference preparation or calibration reagent that eliminates or at least reduces the above-mentioned problems connected to the techniques presently known.

BRIEF DESCRIPTION OF THE DRAWINGS

In FIG. 1A, the equation used is y=x+6.22 $R^2$=1.00. In FIG. 1B, the equation used is ln(FI)=5.87+1*ln(ISU-E) $R^2$=0.99.

FIG. 2A shows a correlation plot for the allergen component Phl p 5. Bivariate fit of ISU/chiplot by kUA/l Phl p 5. Log(ISU/chiplot) =0.1735344+0.8732028*Log(kUA/l). FIG. 2B shows a correlation plot for the allergen component Bet v 1. Bivariate fit of ISU/chiplot by kUA/l Bet v 1. Log(ISU/chiplot) =0.4851362+0.8967003*Log(kUA/1).

TERMS

All terms used in the present specification are intended to have the meaning usually given to them in the art. For the sake of clarity, some terms are further described below.

A "multiplex assay" is construed as meaning a procedure by which analytes of multiple specificities are detected and, in some cases, quantified in a single serum specimen using a single reaction mixture of reagents. For example, a multiplex assay would be one that measures IgE antibody to multiple allergen specificities using a single reaction step. One illustration of a multiplex IgE assay is a chip-based microarrayed test in which individual purified allergens (often recombinant in nature) are adsorbed onto spots in triplicate on a silicon microchip. Incubation of a small quantity of serum with the microarray chip exposes a patient's serum to many different allergen specificities at one time. Following a buffer wash to remove unbound serum proteins, bound IgE is then detected with antihuman IgE conjugate and a subsequent addition of substrate.

The term "capturing agent" is construed as a molecule capable of directly or indirectly binding an analyte of interest. A capturing agent may be an antigen such as an allergen when the analyte is IgE antibodies.

A "detection molecule" is defined as a structure with two essential features, i.e. 1) has a capacity to specifically bind to a calibration agent, and 2) has a common detectable feature. Examples of detection molecules are: an antibody with a variable and a constant region, an aptamer consisting of DNA but with a defined binding structure, a bacterium with a surface antigen that binds and that contains DNA, which can be labeled and detected. Antibodies specific for human IgE are known to be used as detection molecules in total and allergen-specific IgE antibody assays. These key reagents confer the specificity on the assays, and thus they must be highly specific for unique determinants on epsilon-heavy chains. Once purified, the polyclonal or monoclonal antihuman IgE reagent antibodies are either used directly as a solution phase antibody or subjected to chemical modification in the form of radio-labeling, enzyme-labeling, or chemical and physical immobilization on solid-phase matrices.

According to the present invention, a "binding molecule" is construed as meaning a molecule that has two essential features, i.e. 1) a capacity to bind specifically to a capturing agent, and 2) a capacity to bind to a detection molecule. Immunoglobulins and fragments thereof are examples of such binding molecules. Other examples include cellular receptors, soluble receptors and their ligands, and further peptide biomarkers and protein biomarkers, such as antigenic biomarkers.

SUMMARY OF THE INVENTION

The present invention solves the above-mentioned problems related to the calibration of multiplex assays for the detection of binding molecules, such as immunoglobulins alone and/or in combination with other binding molecules.

The present invention provides a method for calibrating a multiplex assay, comprising: adding a calibration reagent to a solid phase on which a plurality of capturing agents are immobilised,
optionally washing the phase to remove unbound calibration reagent,
adding a detection molecule which has a capacity to bind to the calibration reagent,
optionally washing the solid phase to remove unbound detection molecule, detecting bound detection molecule,
thereby creating a calibration curve comprising a number of calibration points/intervals, characterised in that the calibration reagent comprises at least two different binding molecules, wherein each binding molecule has a capacity to bind specifically to a capturing agent immobilised on the solid phase and a capacity to bind to a detection molecule, and wherein at least two of the binding molecules are present at different concentrations in the calibration reagent, thereby representing different calibration points/intervals of the calibration curve.

In one embodiment, the capturing agents are immobilised in a number of spots on the solid phase.

In another embodiment, the solid phase is in the form of beads, on which the capturing agents are immobilised. Such beads may be present in a liquid phase.

In an embodiment of the method, the binding molecules are recombinant antibodies, native antibodies such as autoantibodies, or peptide/protein biomarkers such as antigenic biomarkers.

In a more specific embodiment of the method, the binding molecules are chimeric antibodies, such as mouse-human chimeric antibodies comprising the variable domain of the heavy chain of an allergen-specific monoclonal mouse IgG and a human IgE heavy chain.

In an embodiment of the method, the plurality of capturing agents is at least 5 different capturing agents, such as at least 10, at least 50, or at least 100 different capturing agents.

In an embodiment of the method, the capturing agents are allergen components, such as native or recombinant allergen components, or disease-related antigens, such as antigenic components related to infectious disease or autoimmune disease such as rheumatoid arthritis, or antibodies specific for peptide/protein biomarkers.

In an embodiment of the method, the detection molecule is an anti-immunoglobulin conjugate, such as an antihuman IgE conjugate or an antihuman IgG conjugate, or is an antibody specific for a peptide/protein biomarker.

In an embodiment of the method, the binding molecules are recombinant antibodies, preferably chimeric IgE antibodies, the capturing agents are allergen components, such as native or recombinant allergen components, and the detection molecule is an antihuman IgE conjugate.

In another embodiment of the method, the binding molecules are native antibodies, preferably IgG autoantibodies, the capturing agents are disease-related antigens, such as antigenic components related to infectious or autoimmune disease, preferably autoimmune disease, and the detection molecule is an antihuman IgG conjugate.

In yet another embodiment of the method, the binding molecules are peptide/protein biomarkers, preferably biomarkers for prostate cancer, the capturing agents are antibodies specific for said peptide/protein biomarkers, and the detection molecules are antibodies specific for said peptide/protein biomarkers.

In an embodiment of the method, the calibration reagent comprises at least 5, such as at least 10, such as at least 15 different binding molecules, such as recombinant antibodies, native antibodies such as autoantibodies, or peptide/protein biomarkers.

In a more specific embodiment of the method, the calibration reagent comprises at least 5, preferably at least 10, more preferably at least 15 different chimeric IgE antibodies, wherein each chimeric antibody has a capacity to bind specifically to an allergen component selected from the group consisting of Bet v 1, Der p 2, Ole e 1, Gal d 1, Art v 1, Fel d 1, Phl p 1, Amb a 1, Can f 1, Der p 1, Gal d 2, Can f 2, Can f 5, Phl p 5 and Pru p 3.

In an embodiment of the method, the multiplex assay is performed on a microarray chip.

According to a second aspect of the present invention, a multiplex assay system is provided for detection of a molecule of interest, such as (a) an immunoglobulin or (b) a peptide/protein biomarker present in a biological sample, comprising:
a reaction vessel,
a plurality of capturing agents immobilised on a solid phase,
a detection molecule, such as (a) an anti-immunoglobulin detection molecule or (b) a detection molecule binding to a peptide/protein biomarker,
a calibration reagent,
a reaction buffer medium,
characterised in that the calibration reagent comprises at least two different binding molecules, wherein each binding molecule has a capacity to bind specifically to a capturing agent immobilised on the solid phase and a capacity to bind to the detection molecule, and wherein at least two of the binding molecules are present at different concentrations in the calibration reagent.

The reaction vessel may be in the form of a plastic (polyethylene) or glass tube, plastic microtiter plate well, plastic stick, polyethylene cap with an internal sponge matrix, and carbohydrate filament-coated silicone chip.

In an embodiment, the capturing agents are immobilised in a number of spots on the solid phase. Alternatively, the solid phase is in the form of beads on which the capturing agents are immobilised. Such beads may be present in a liquid phase.

In an embodiment of the system, the molecule of interest is (i) an IgE antibody or (ii) an IgG antibody, or (iii) a peptide/protein biomarker for disease such as cancer.

In an embodiment of the system, the detection molecule is (i) an anti-human IgE conjugate, (ii) an anti-human IgG conjugate, or (iii) an antibody specific for a peptide/protein biomarker.

In an embodiment of the system, the biological sample is a human serum or plasma sample.

In an embodiment of the system, the calibration reagent comprises at least 5, such as at least 10, such as at least 15 different binding molecules.

In an embodiment of the system, the binding molecules are recombinant antibodies, such as chimeric antibodies, native antibodies such as autoantibodies, or peptide/protein biomarkers.

In an embodiment of the system, the capturing agents are allergen components, such as native or recombinant allergen components, or disease-related antigens, such as antigenic components related to infectious disease, or antigenic components related to autoimmune disease, or antibodies specific for peptide/protein biomarkers.

In an embodiment of the system, the binding molecules are recombinant antibodies, preferably chimeric IgE antibodies, the capturing agents are allergen components, such as native or recombinant allergen components, and the detection molecule is an antihuman IgE conjugate.

In another embodiment of the system, the binding molecules are native antibodies, preferably IgG autoantibodies, the capturing agents are disease-related antigens, such as antigenic components related to infectious or autoimmune disease, preferably autoimmune disease, and the detection molecule is an antihuman IgG conjugate.

In yet another embodiment of the system, the binding molecules are peptide/protein biomarkers, preferably biomarkers for prostate cancer, the capturing agents are antibodies specific for said peptide/protein biomarkers, and the detection molecules are antibodies specific for said peptide/protein biomarkers.

In an embodiment of the system, the calibration reagent comprises fifteen different mouse-human chimeric IgE antibodies, wherein each chimeric antibody has a capacity to bind specifically to an allergen component selected from the group consisting of Bet v 1, Der p 2, Ole e 1, Gal d 1, Art v 1, Fel d 1, Phl p 1, Amb a 1, Can f 1, Der p 1, Gal d 2, Can f 2, Can f 5, Phl p 5 and Pru p 3.

The present invention further provides a calibration reagent comprising at least two different chimeric antibodies, wherein each binding molecule has the capacity to bind specifically to at least one of the allergen components listed in the appended Table 1.

In an embodiment, the calibration reagent comprises at least 5, such as at least 10, such as at least 15 different mouse-human chimeric IgE antibodies.

In another embodiment, each mouse-human chimeric IgE antibody of the calibration reagent has the capacity to bind specifically to an allergen component selected from the group consisting of Bet v 1, Der p 2, Ole e 1, Gal d 1, Art v 1, Fel d 1, Phl p 1, Amb a 1, Can f 1, Der p 1, Gal d 2, Can f 2, Can f 5, Phl p 5 and Pru p 3.

In an embodiment, the calibration reagent consists of fifteen different mouse-human chimeric IgE antibody solutions, wherein each chimeric antibody has the capacity to bind specifically to an allergen component selected from the group consisting of Bet v 1, Der p 2, Ole e 1, Gal d 1, Art v 1, Fel d 1, Phl p 1, Amb a 1, Can f 1, Der p 1, Gal d 2, Can f 2, Can f 5, Phl p 5 and Pru p 3.

The calibration reagent according to the present invention may optionally comprise a preservative, such as Kathon CG or sodium azide, or other preservatives known to the person skilled in the art.

The present invention further provides a kit comprising a calibration reagent as described above, which is adapted for use in a calibration method as described above.

Further, the present invention provides a method for producing a calibration reagent for a multiplex assay, comprising providing at least two different binding molecules, wherein each binding molecule has a capacity to bind specifically to a capturing agent immobilised on a solid phase of the assay and a capacity to bind to a detection molecule, adjusting the concentration of said binding molecules to the relevant measuring range of the assay, preparing a mixture of said binding molecules, thereby obtaining a calibration reagent.

DETAILED DESCRIPTION OF THE INVENTION

The present invention provides a time-efficient and accurate calibration method and a calibration reagent, comprising a mixture of calibration molecules, including a multitude of antigens and/or biomarker binding sites in a multiplex setting. According to the present invention, all calibration molecules have been combined into one single calibration sample and it is shown that several binding molecules present in the same solution, including binding molecules of different concentrations as well as of different specificities, can be utilized.

At present, in a common situation with 6 different immunoassays (target calibration molecules) requiring 5 calibration concentrations each it would require the analysis of 6×5=30 different assays to be run. By use of the present invention, this is reduced to a minimum. In addition, the analysis of a set of combined calibration molecules present at different concentrations allows for the possibility to establish the relative interrelation between the different binding molecules without the potentially systematic assay system variability that may be the result of the 30 different individual assays needed to be analyzed. This invention can thereby reduce the number of concentration intervals necessary to fulfill the calibration requirements and quality required as compared to a traditional singleplex assay.

The present invention will now be described in more detail by referring to three specific embodiments of the invention:

1) Analysis of specific IgE antibodies, wherein the calibration reagent comprises at least two different chimeric IgE antibodies, each of which has a capacity to specifically bind to an allergenic component immobilised on a microarray chip to be calibrated.

2) Detection of specific IgG autoantibodies, wherein the calibration reagent comprises at least two different IgG antibodies, each of which has a capacity to specifically bind to an antigenic component (such as peptides or proteins) immobilised on a microarray chip to be calibrated.

3) Detection of peptide/protein biomarkers, wherein the calibration reagent comprises at least two different peptide/protein biomarkers. On a microarray chip to be calibrated, antibodies are immobilised. Each of said antibodies is capable of binding specifically to one type of the peptide/protein biomarkers.

Example 1

This method is used to create a calibration curve for the quantitation of specific IgE antibodies present in allergic individuals. The calibrator consists of a sample containing binding molecules in the form of chimeric IgE antibodies in a buffer. Each of the chimeric IgE antibodies has a different specificity, and the chimeric IgE antibodies are present in different concentrations in the sample.

For the preparation of chimeric antibodies, mouse cell lines are used to produce monoclonal IgG antibodies. The exon and the intron for the variable domain of the heavy chain of an allergen specific monoclonal IgG antibody is cloned and inserted into an expression vector together with the signal sequence and the coding sequence for a human IgE heavy chain. The expression vector is transformed into an Sp 2/0 myeloma cell line, resulting in the expression of an allergen specific human IgE heavy chain. The Sp 2/0 cells that produce the IgE heavy chain are fused with a hybridoma cell line which expresses the IgG heavy chain and light chain, and from which the variable domain was initially cloned. Fused cells, which correctly express a chimeric IgE antibody, comprising a human IgE heavy chain and a mouse IgG light chain, are identified by use of ELISA comprising the relevant allergen and an anti-IgE conjugate. Preferably, only cell clones which exclusively produce IgE antibodies and have lost the ability to produce the IgG heavy chain are selected for the production of chimeric antibodies.

An alternative method for preparing chimeric antibodies comprises transforming an expression vector in accordance with the above description directly into the hybridoma cell line from which the variable domain was initially cloned. The IgE positive hybridoma clones thus created will produce IgG antibodies in addition to IgE. The IgE antibodies may be purified by affinity chromatography on an anti-IgE column (Bohman et al 2007, Allergy, Vol 62, supplement 83, p. 49).

The concentration in a solution of a chimeric antibody thus produced and purified may be determined by use of the IMMUNOCAP® sIgE assay, which, as previously mentioned, is standardised against the WHO reference preparation 75/502 for IgE (Hamilton R G, see above).

When the concentration has been determined by use of the quantitative IMMUNOCAP® sIgE assay, expressed as $kU_A/l$, such a solution of a chimeric antibody is then run on the semiquantitative IMMUNOCAP ISAC® sIgE assay to determine the concentration of the chimeric antibody in said assay, expressed as arbitrary units, ISU-E.

According to the present invention, the IMMUNOCAP ISAC® sIgE assay is calibrated by use of a calibration reagent comprising solutions of several chimeric antibodies, the defined concentrations of which have been determined in the IMMUNOCAP® system.

Each chimeric antibody to be used in the calibration reagent is diluted individually in a serum depleted of specific IgE antibodies (a so-called negative serum) into the clinically relevant measuring range of 0.3-100 ISU-E. 1 $kU_A/l$ corresponds to 2.42 ng sIgE/ml, which is used to calculate the dilution factor for each chimeric antibody.

Figure 2A:
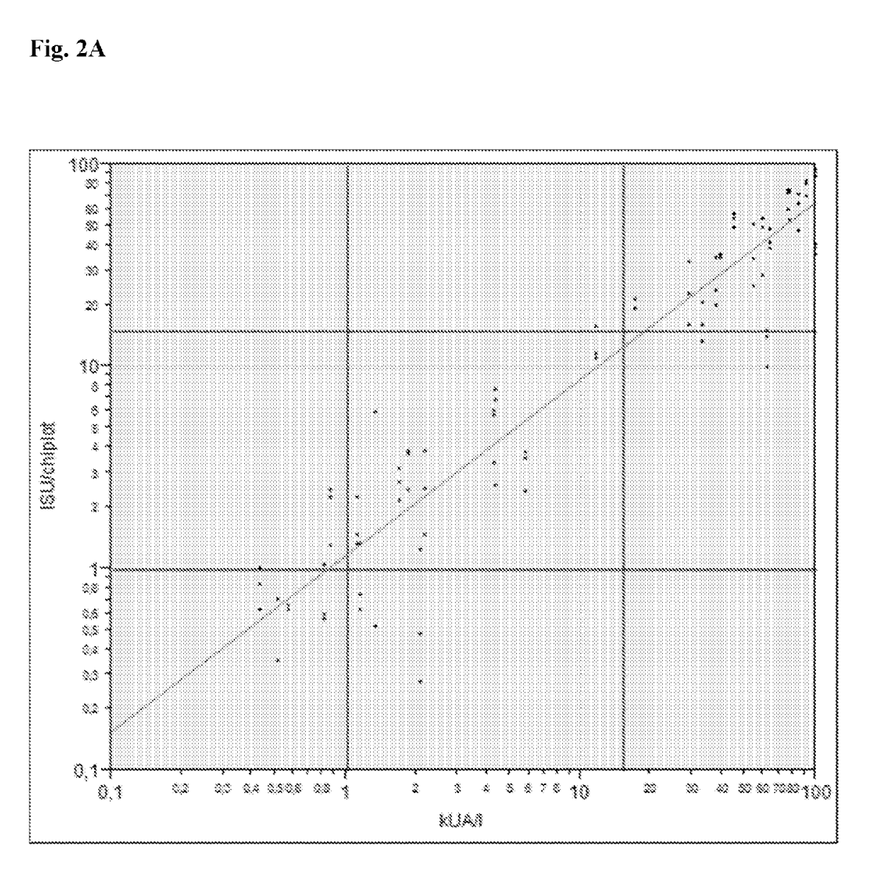
FIG. 2A and FIG. 2B show correlation plots for different allergen components, where a calibration reagent according to Example 1 (below) has been used to calculate the ISU-E values. The straight line symbolises a transformed fit log to log. The black dots in the figure represent IgE antibody specific for Phl p 5 (FIG. 2A) and for Bet v 1 (FIG. 2B), respectively, detected in patients' samples run on IMMUNOCAP ISAC® sIgE assay and compared to the reference method, IMMUNOCAP® sIgE assay.
Figure 2B:
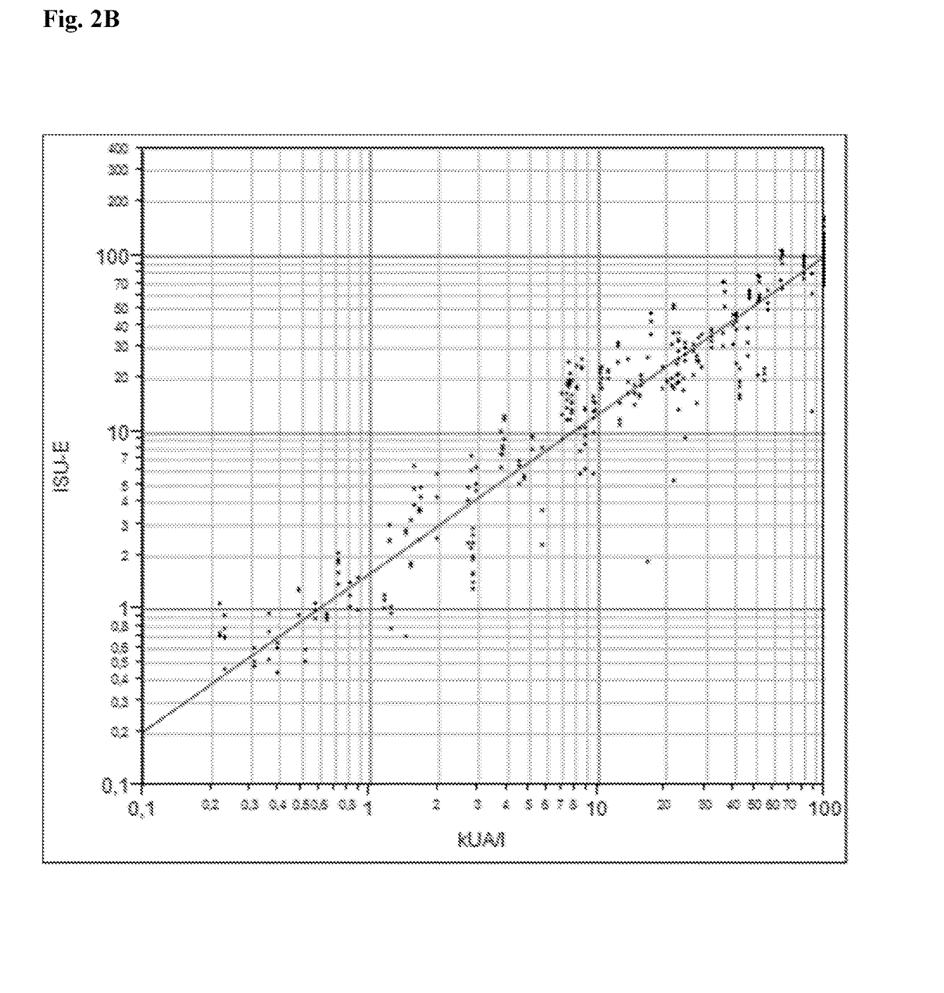

As an alternative to negative serum, a buffer may be used for the dilution of chimeric antibodies. For example, buffers used in the IMMUNOCAP® assay could be used for the dilution, and could thus be a part of the calibration reagent according to the present invention. The IMMUNOCAP® value ($kU_A/l$) and the IMMUNOCAP ISAC® value (ISU-E) for a specific IgE antibody, as detected in patients' samples, may be plotted against each other in a graph, giving evidence that the concept of chimeric calibration according to the present invention is valid. Such a correlation plot is illustrated by the straight line in FIG. 2A and FIG. 2B, respectively ($kU_A/l$ on the x-axis and ISU-E on the y-axis).

A calibration reagent according to the present invention is obtained by:
  determining at least two calibration points within the clinically relevant measuring range, preferably at least three, more preferably at least four calibration points;
  using at least one chimeric antibody per calibration point, preferably at least two, more preferably at least three or four chimeric antibodies;
  choosing the calibration points such that all calibration points give more or less the same response measured as fluorescence intensity (FI) in the IMMUNOCAP ISAC® assay, i.e. such that all the solutions of chimeric antibodies used have fairly equal concentrations.

As mentioned above, the IMMUNOCAP ISAC® assay is semi-quantitative, presenting the results in four classes (0=Undetectable or Very Low, 1=Low, 2=Moderate to High, 3=Very High).

Each calibration point can in principle be located anywhere in the measuring range. However, since the test is semi-quantitative, it is advantageous to choose calibration points at end points of at least some of the classes. ISU-E values below 0.3 belong to Class 0; ISU-E values from 0.3 to 1.0 are Class 1; class 2 indicates ISU-E values from 1.0 to 15.0; and ISU-E values above 15 belong to class 3. Preferably, one calibration point is located at 1 ISU-E and another calibration point is located at 15 ISU-E.

Further, the calibration points are preferably spread out fairly evenly over the entire measuring range. Therefore, two more calibration points are chosen to cover the remaining parts of the measuring range. Most preferably, said further two calibration points are located at 4 ISU-E and 50 ISU-E, respectively.

A calibration reagent according to the present invention was produced as follows. Fifteen different chimeric antibody solutions were used, each specific for one of the following allergens:

TABLE 2

| Allergen specific chimeric IgE antibodies |
| --- |
| Anti-Gal d 1 Ovomucoid |
| Anti-Gal d 2 Ovalbumin |
| Anti-Phl p1 |
| Anti-Phl p 5 |
| Anti-Bet v 1 |
| Anti-Fel d1 |
| Anti-Der p1 |
| Anti-Der p2 |
| Anti-Amb a1 |
| Anti-Ole e 1 |
| Anti-Art v 1 |
| Anti-Can F1 |
| Anti-Can F2 |
| Anti-Can F5 |
| Anti-Pru p 3 |

The allergen specific chimeric antibodies in Table 2 were mouse-human chimeric antibodies, each comprising the variable domain of the heavy chain of an allergen-specific monoclonal mouse IgG and a human IgE heavy chain.

The concentrations of said antibody solutions were first determined by use of the IMMUNOCAP® assay (giving values in $kU_A/l$), and the corresponding ISU-E values were established by running the solutions on the IMMUNOCAP ISAC® assay.

Four calibration points were to be determined, using three or four chimeric antibodies for each calibration point, as follows:
Point a, 1.0 ISU-E: Bet v 1, Der p 2, Ole e 1, Gal d 1.
Point b, 4.0 ISU-E: Art v 1, Fel d 1, Phl p 1.
Point c, 15.0 ISU-E: Amb a 1, Can f 1, Der p 1, Gal d 2.
Point d, 50 ISU-E: Can f 2, Can f 5, Phl p 5, Pru p 3.

Each chimeric antibody solution was diluted such that it would give the above-mentioned desired ISU-E value (Table 3). The dilution medium used was human serum depleted of specific IgE.

TABLE 3

| Dilution protocol for the chimeric IgE antibodies of the calibration reagent | |
| --- | --- |
| ISU Chimeric lot | Dilution factor 1/X |
| 1_Bet v 1_009125 | 10114 |
| 1_Der p 2_011571 | 5088 |
| 1_Gal d 1_011534 | 2968 |
| 1_Ole e 1_006381 | 6033 |
| 4_Art v 1_009834 | 1822 |
| 4_Fel d 1_07128 | 10602 |
| 4_Phl p 1_007121 | 1855 |
| 15_Amb a 1_06310 | 1865 |
| 15_Can f 1_009119 | 1004 |

TABLE 3-continued

Dilution protocol for the chimeric
IgE antibodies of the calibration reagent

| ISU Chimeric lot | Dilution factor 1/X |
|---|---|
| 15_Der p 1_007121 | 948 |
| 15_Gal d 2_011583 | 58 |
| 50_Can f 2_009844 | 344 |
| 50_Can f 5_009853 | 2513 |
| 50_Phl p 5_007132 | 825 |
| 50_Pru p 3_012813 | 953 |

After individual dilution of each chimeric antibody, all fifteen chimeric antibody solutions were mixed together, thus obtaining a calibration reagent according to the present invention.

Figure 1A:
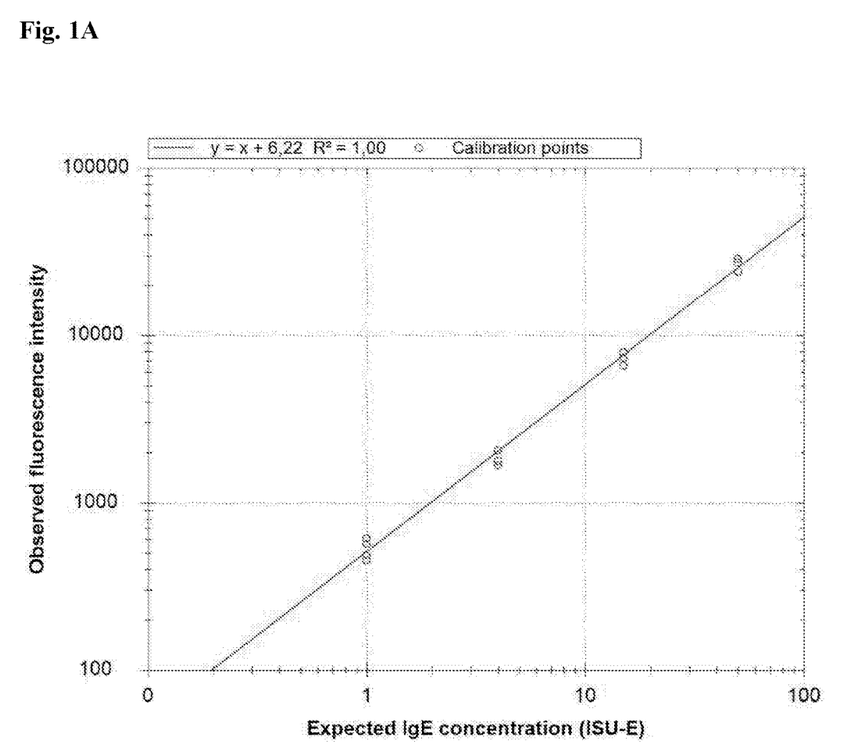
FIG. 1A and FIG. 1B show calibration curves obtained by performing the IMMUNOCAP ISAC® sIgE assay on a calibration reagent comprising 15 different chimeric antibodies in accordance with Example 1 (below). The four calibration points are located at 1.0, 4.0, 15.0 and 50 ISU-E. The calibration curves give the correlation between the observed fluorescence intensity (y-axis) and ISAC Standardized Units for specific IgE (ISU-E), Arbitrary Units (x-axis). The dots depicted in the diagram represent the calibration points.
Figure 1B:
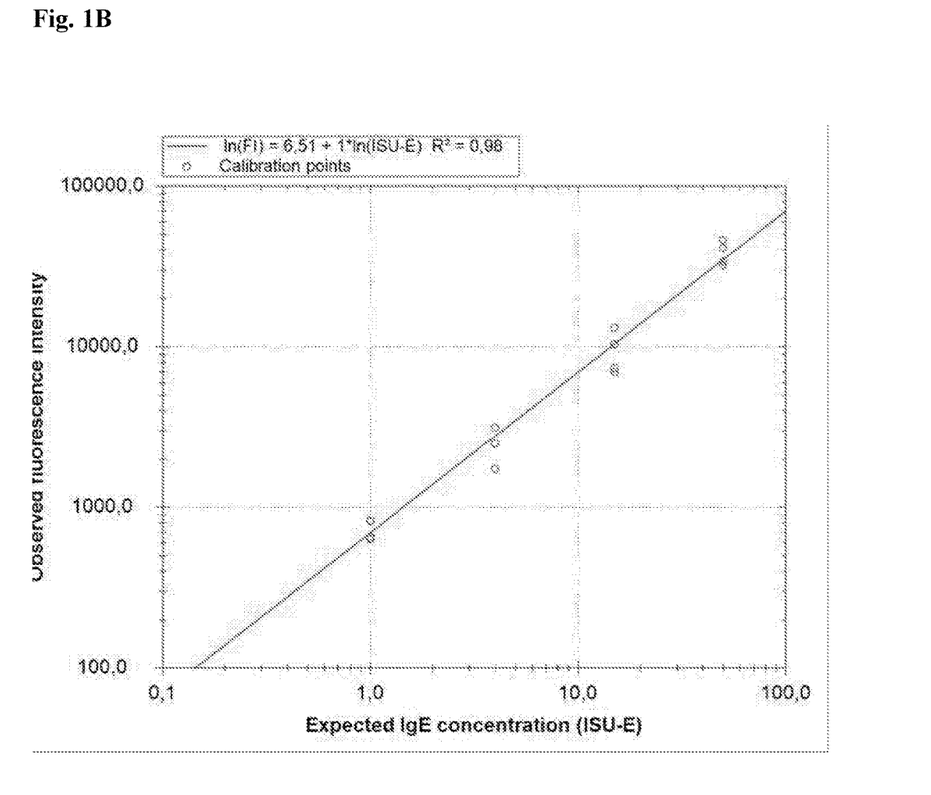

The calibration reagent was used to create a calibration curve according to FIG. 1A and FIG. 1B, respectively, showing the correlation between the observed fluorescence intensity (y-axis) and ISAC Standardized Units for specific IgE (ISU-E), Arbitrary Units (x-axis).

When the calibration reagent is added to an ImmunoCAP ISAC® sIgE microarray chip, the fifteen chimeric antibodies described above will bind to the fifteen allergen components, for which said chimeric antibodies have specificity. In addition, however, the chimeric antibodies will also cross-react with further allergen components immobilised on the microarray chip, which have similar structures to any one of the fifteen allergen components.

Optionally, such further allergen components may therefore be used as a control for the calibration reagent, and there will be no need for a separate control sample. In this example, three further allergens were used as a control:

At a low level of fluorescence intensity (an ISU-E value below 1.0): Mal d 1 or Acd 8
Moderate level (1-15 ISU-E): Der f 1, Pla a 2 or Pla a 3
High level (>15 ISU-E): Art v 3

The detection molecule used in the assay was an antihuman IgE conjugate.

Example 2

This method was used to create a calibration curve for the quantitation of specific IgG antibodies present in patients having rheumatoid arthritis (RA). The calibrator consisted of a sample containing binding molecules in the form of IgG autoantibodies of different specificities and of different concentrations. This is analogous to the IgE calibrator described in Example 1 above, except that the sample consisted of a pool of different human sera from RA patients. Here, the sera from five different patients were pooled. It could however be a smaller or larger number of sera that are pooled, as long as the resulting sample contains the various different specificities of IgG antibodies representing various concentrations covering the required number of calibration points/intervals.

The RA calibrator consisted of five different sera of the following volumes:
Serum 1=5 μL
Serum 2=5 μL
Serum 3=5 μL
Serum 4=10 μL
Serum 5=5 μL
Total volume=30 μL The serum pool was diluted 1:50 in diluent for the ISAC assay.

Capturing agents in the form of antigenic components (such as peptides or proteins) relevant for RA are immobilised on a microarray chip. Here, 32 different antigens were immobilised (antigens no. 1-32 in Table 4).

The detection molecule used in the assay was an antihuman IgG conjugate.

TABLE 4

Antigens immobilized on the microarray chip.

| Antigen no. | Arbitrary Units |
|---|---|
| 1 | 38 |
| 2 | 41 |
| 3 | 43 |
| 4 | 47 |
| 5 | 88 |
| 6 | 93 |
| 7 | 97 |
| 8 | 98 |
| 9 | 101 |
| 10 | 103 |
| 11 | 142 |
| 12 | 174 |
| 13 | 336 |
| 14 | 446 |
| 15 | 487 |
| 16 | 564 |
| 17 | 595 |
| 18 | 652 |
| 19 | 691 |
| 20 | 1259 |
| 21 | 1325 |
| 22 | 1389 |
| 23 | 2293 |
| 24 | 2692 |
| 25 | 2706 |
| 26 | 2918 |
| 27 | 3226 |
| 28 | 3344 |
| 29 | 4008 |
| 30 | 4394 |
| 31 | 4597 |
| 32 | 4722 |

Figure 3:
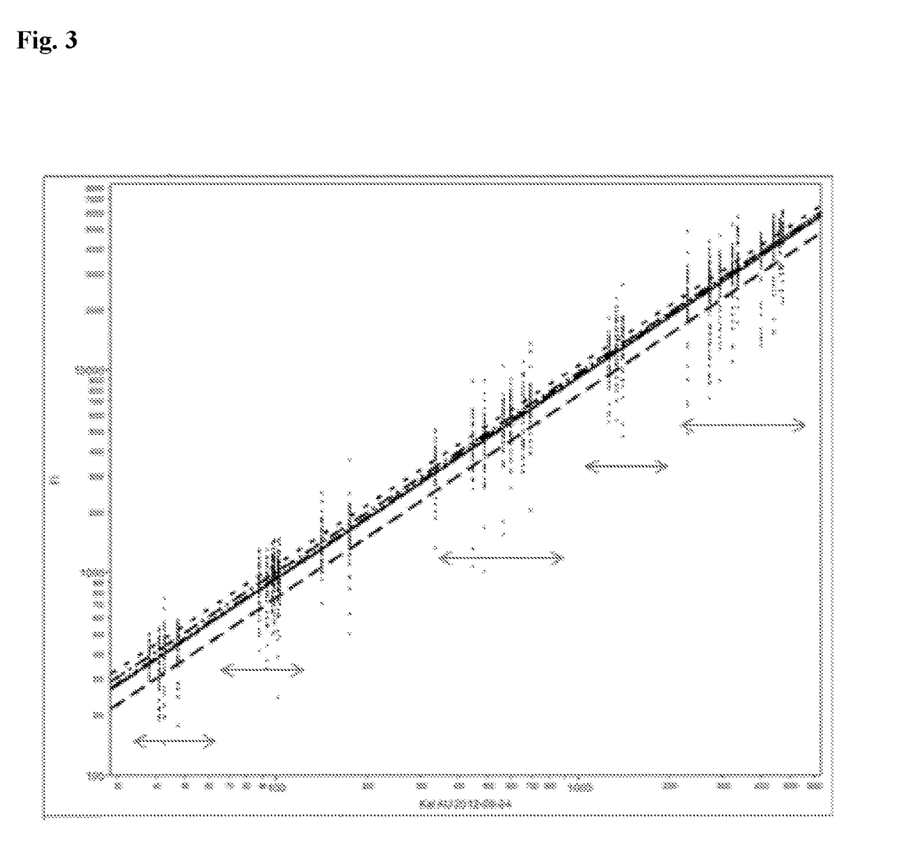
FIG. 3 shows five calibration curves obtained by performing the IMMUNOCAP ISAC® sIgG assay five times on a calibration reagent comprising five pooled human sera from patients having rheumatoid arthritis, in accordance with Example 2 (below). The calibration curves give the correlation between the observed fluorescence intensity (y-axis) and ISAC Standardized Units for specific IgG, Arbitrary Units (x-axis) in a log/log plot. The arrows in the figure represent the selected target calibration intervals/points.
Figure 4:
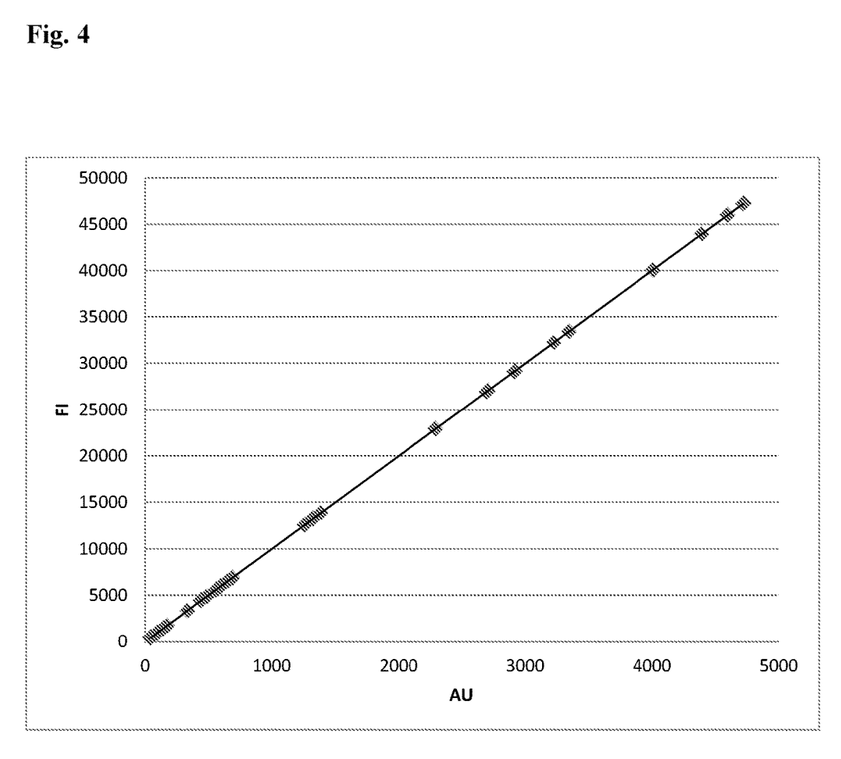
FIG. 4 shows median values of the observed fluorescence intensity (y-axis) and ISAC Standardized Units for specific IgG, Arbitrary Units (x-axis) in a ln/ln plot, based on the results shown in FIG. 3.

The calibration reagent was used to create the calibration curves according to FIG. 3, showing the correlation between the observed fluorescence intensity (y-axis) and ISAC Standardized Units for specific IgG, Arbitrary Units (x-axis) log/log plot. In this example we have analysed the calibration sample five times and FIG. 3 shows the tight correlation between the 5 different times the sample was analysed. The 32 different antigens were bound with patient serum immunoglobulins selected and diluted in such way that the full curve range was covered. The arrows in the figure represent the selected target calibration intervals/points. FIG. 4 shows median values of the observed fluorescence intensity (y-axis) and ISAC Standardized Units for specific IgG, Arbitrary Units (x-axis) in a ln/ln plot, based on the results shown in FIG. 3, and generating a very stable calibration curve utilizing all 32 values ensuring that the integrity of each variable in the array is intact.

Example 3

This method was used to create a calibration curve for the quantitation of peptide/protein components, which are used as biomarkers for the diagnosis of prostate cancer in men. The calibrator consisted of a sample containing binding molecules in the form of different peptide/protein biomarkers of different concentrations.

Capturing agents in the form of antibodies specific for the different peptide/protein components relevant for prostate cancer were immobilised on a microarray chip.

The detection molecules used in the assay were secondary antibodies specific for different epitopes on the antigenic components (i.e. the binding molecules) than the epitopes for which the immobilised antibodies (i.e. the capturing agents) were specific.

Figure 5:
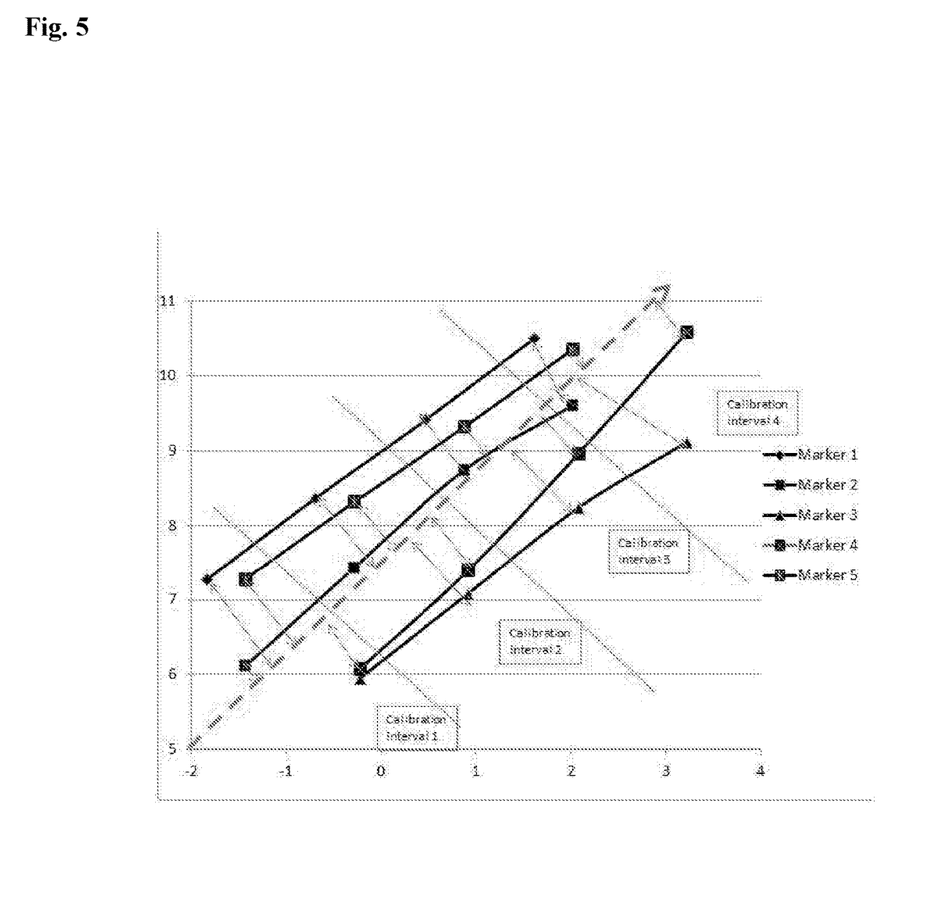
FIG. 5 shows five calibration curves obtained by performing the IMMUNOCAP ISAC® antigen biomarker assay on a calibration reagent comprising five different antigenic biomarkers for prostate cancer, in accordance with Example 3 (below). The calibration curves give the correlation between the observed fluorescence intensity (y-axis) and ISAC Standardized Units for the antigenic biomarkers, Arbitrary Units (x-axis). Four different calibration intervals, divided by thin dotted lines, are depicted in the figure. The diagonal, bold dotted arrow represents a calculated average based on the interrelation between all 20 standard points. The thin arrows stretching between the calibration curves and the bold dotted arrow illustrate that each calibration curve independent of dynamic range and concentration interval can be described as a function of, in this case, all 20 different standard points.

The calibration reagent was used to create a calibration curve according to FIG. 5, showing the correlation between the observed fluorescence intensity (y-axis) and ISAC Standardized Units for the antigenic biomarkers, Arbitrary Units (x-axis).

FIG. 5 represents an example which explain how the interrelation between biomarkers with different concentration spans can be interlinked as the biomarkers are analyzed on a single array and thereby minimizing the use of a multitude of different concentrations. All detected concentrations form a common average that is used to recalculate the actual concentration. These calculations should be optimized for each set of unique group of biomarkers analyzed simultaneously on a single array. Here, five different peptide/protein components were used and analysed in four different concentrations as compared to the present methods for singleplex PSA assays that normally require 6 different standard points. In fact, we hereby have significantly reduced the number of single analyses and increased the precision by using all 20 standard points to define the calibration curves for the five different assays. Four different calibration intervals, divided by thin dotted lines, are depicted in the figure. The diagonal, bold dotted arrow represents a calculated average based on the interrelation between all 20 standard points. The thin arrows stretching between the calibration curves and the bold dotted arrow illustrate that each calibration curve independent of dynamic range and concentration interval can be described as a function of, in this case, all 20 different standard points. This allows an improved precision as compared to the normally present 6 individual calibration points for a single assay using fewer calibration sample concentrations.

The reason for using several binding molecules (e.g. recombinant antibodies, such as chimeric antibodies (Example 1), human IgG autoantibodies (Example 2), or peptide/protein biomarkers (Example 3)) for each calibration point is to decrease possible variations in the calibration due to variations in the immobilisation of the capturing agents (e.g. allergen components (Example 1), antigens to which human IgG autoantibodies bind (Example 2), or antibodies specific for peptide/protein biomarkers of interest (Example 3), which may occur during manufacture of the microarray chip. Thus, even if one or two components would deviate from the expected value, this would not markedly influence the calibration curve.

The calibration curve may be in the form of a linear approximation (as shown in FIG. 1 for example) or a sigmoid curve. It is also within the scope of the present invention to use a larger number of binding molecules (e.g. recombinant antibodies, such as chimeric antibodies (Example 1), human IgG autoantibodies (Example 2), or peptide/protein biomarkers (Example 3)) and determine several different calibration curves, thereby further compensating for differences in the curve form due to varying properties of the capturing agents (e.g. allergen components (Example 1), antigens to which human IgG autoantibodies bind (Example 2), or antibodies specific for peptide/protein biomarkers of interest (Example 3).

The examples above illustrate the present invention relating to a calibration reagent, its method of production and its uses. The examples are only illustrative and should not be considered as limiting the invention, which is defined by the scope of the appended claims.

TABLE 1

Allergenic components that may be used in a multiplex assay

| SOURCE | COMPONENT | Recombinant/ Native | PROTEIN FAMILY OR FUNCTION |
|---|---|---|---|
| Kiwi | Act d 1 | N | Cysteine protease |
| | Act d 2 | N | Thaumatin-like protein |
| | Act d 5 | N | Kiwellin |
| | Act d 8 | R | PR-10 |
| Alder | Aln g 1 | R | PR-10 |
| *Alternaria* | Alt a 1 | R | Acidic glycoprotein |
| | Alt a 6 | R | Enolase |
| Ragweed | Amb a 1 | N | Pectate lyase |
| Cashew nut | Ana o 2 | R | Storage protein, 2S albumin |
| *Anisakis* | Ani s 1 | R | Serine protease inhibitor |
| | Ani s 3 | R | Tropomyosin |
| Celery | Api g 1 | R | PR-10 |
| Bee | Api m 1 | R | Phospholipase A2 |
| | Api m 4 | N | Melittin |
| Peanut | Ara h 1 | R | Storage protein, 7S globulin |
| | Ara h 2 | R | Storage protein, 2S albumin |
| | Ara h 3 | R | Storage protein, 11S globulin |
| | Ara h 6 | N | Storage protein, 2S albumin |
| | Ara h 8 | R | PR-10 |
| | Ara h 9 | R | LTP |
| Mugwort | Art v 1 | N | Defensin |
| | Art v 3 | N | LTP |
| *Aspergillus* | Asp f 1 | R | Mitogillin family |
| | Asp f 3 | R | Peroxysomal protein |
| | Asp f 6 | R | Mn superoxide dismutase |
| Brazil nut | Ber e 1 | R | Storage protein, 2S albumin |
| Birch | Bet v 1 | N | PR-10 |
| | Bet v 2 | R | Profilin |
| | Bet v 4 | R | Polcalcin |
| Cockroach | Bla g 1 | R | Cockroach group 1 |
| | Bla g 2 | R | Aspartic protease |

TABLE 1-continued

Allergenic components that may be used in a multiplex assay

| SOURCE | COMPONENT | Recombinant/ Native | PROTEIN FAMILY OR FUNCTION |
|---|---|---|---|
|  | Bla g 5 | R | Glutathione S-transferase |
|  | Bla g 7 | N | Tropomyosin |
| *Blomia* | Blo t 5 | R |  |
| Milk | Bos d 4 | N | Alpha-lactalbumin |
|  | Bos d 5 | N | Beta-lactoglobulin |
| Cow | Bos d 6 | N | Serum Albumin |
| Milk | Bos d 8 | N | Caseins |
|  | Bos d Lactoferrin | N | Transferrin |
| Dog | Can f 1 | R | Lipocalin |
|  | Can f 2 | R | Lipocalin |
|  | Can f 3 | N | Serum Albumin |
|  | Can f 5 | R | Arginine Esterase |
| Goosefoot | Che a 1 | R | Trypsin Inhibitor |
| *Cladosporium* | Cla h 8 | R | Mannitol dehydrogenase |
| Hazel | Cor a 1.0101 | R | PR-10 |
| Hazelnut | Cor a 1.0401 | R | PR-10 |
|  | Cor a 8 | R | LTP |
|  | Cor a 9 | N | Storage protein, 11S globulin |
| Japanese cedar | Cry j 1 | N | Pectate lyase |
| Cypress | Cup a 1 | N | Pectate lyase |
| Bermuda | Cyn d 1 | N | Grass group 1 |
|  | Der f 1 | N | Cysteine protease |
|  | Der f 2 | R | NPC2 family |
| *Dermatophagoides* | Der p 1 | N | Cysteine protease |
|  | Der p 2 | R | NPC2 family |
|  | Der p 10 | R | Tropomyosin |
| Horse | Equ c 1 | R | Lipocalin |
|  | Equ c 3 | N | Serum Albumin |
| Buckwheat | Fag e 2 | N | Storage protein, 2S albumin |
| Cat | Fel d 1 | R | Uteroglobin |
|  | Fel d 2 | N | Serum Albumin |
|  | Fel d 4 | R | Lipocalin |
| Cod | Gad c 1 | R | Parvalbumin |
| Egg white | Gal d 1 | N | Ovomucoid |
|  | Gal d 2 | N | Ovalbumin |
|  | Gal d 3 | N | Conalbumin |
| Egg yolk/chicken | Gal d 5 | N | Livetin (Serum Albumin but species specific) |
|  | Gly m 4 | R | PR-10 |
|  | Gly m 5 | N | Storage protein, Beta-conglycinin |
|  | Gly m 6 | N | Storage protein, Glycinin |
| Latex | Hev b 1 | R | Rubber elongation factor |
|  | Hev b 3 | R | Small rubber particle protein |
|  | Hev b 5 | R | Acidic protein |
|  | Hev b 6.01 | R | Hevein |
|  | Hev b 8 | R | Profilin |
| Walnut | Jug r 1 | N | Storage protein, 2S albumin |
|  | Jug r 2 | N | Vicilin seed storage protein |
|  | Jug r 3 | N | LTP |
| *Lepidoglyphus* | Lep d 2 | R | NPC2 family |
| Apple | Mal d 1 | R | PR-10 |
| Mercury | Mer a 1 | R | Profilin |
| Mouse | Mus m 1 | N | Lipocalin |
|  | MUXF3 | N | CCD |
| Olive | Ole e 1 | N | Trypsin inhibitor |
|  | Ole e 7 | N | LTP |
|  | Ole e 9 | R | Glucanase |
| Wall pellitory | Par j 2 | R | LTP |
| Shrimp | Pen m 1 | N | Tropomyosin |
|  | Pen m 2 | N | Arginine kinase |
|  | Pen m 4 | N | Sarcoplasmic Ca binding Protein |
| Timothy | Phl p 1 | R | Grass group 1 |
|  | Phl p 2 | R | Grass group 2 |
|  | Phl p 4 | N | Berberine bridge enzyme |
|  | Phl p 5b | R | Grass group 5 |
|  | Phl p 6 | R | Grass group 6 |
|  | Phl p 7 | R | Polcalcin |
|  | Phl p 11 | R | Trypsin inhibitor |
|  | Phl p 12 | R | Profilin |
| Plane | Pla a 1 | R | Invertase Inhibitor |
|  | Pla a 2 | N | Polygalacturonases |
|  | Pla a 3 | R | LTP |
| Plantain | Pla l 1 | R | Pectate lyase |
| Paper wasp | Pol d 5 | R | Ag 5 |

TABLE 1-continued

Allergenic components that may be used in a multiplex assay

| SOURCE | COMPONENT | Recombinant/ Native | PROTEIN FAMILY OR FUNCTION |
|---|---|---|---|
| Peach | Pru p 1 | R | PR-10 |
|  | Pru p 3 | R | LTP |
| Saltwort | Sal k 1 | N | Pectin methylesterase |
| Sesame | Ses i 1 | N | Storage protein, 2S albumin |
| Wheat | Tri a 14 | R | LTP |
|  | Tri a 19.0101 | N | Omega 5 gliadin |
|  | Tri a aA_TI | N | Alpha-Amylase/Trypsin Inhibitors |
| Wasp | Ves v 5 | R | Ag 5 |

The invention claimed is:

1. A method for calibrating a multiplex assay operable to detect a plurality of different analytes in a sample, comprising:
providing a solid phase with a plurality of capturing agents for the plurality of different analytes, respectively, immobilised on the solid phase,
adding a calibration reagent to the solid phase on which the plurality of capturing agents are immobilised, wherein the calibration reagent comprises at least two different binding molecules, wherein each binding molecule has a capacity to bind specifically to one of the plurality of capturing agents immobilised on the solid phase, wherein at least two of the binding molecules have different specificities, and wherein of said at least two binding molecules, a first binding molecule is present in a first concentration and a second binding molecule is present in a second concentration, different from the first concentration,
adding a first detection molecule to the solid phase, wherein each binding molecule has a capacity to bind to the first detection molecule,
detecting the bound first detection molecule, and
creating a single calibration curve comprising a plurality of calibration points, wherein the plurality of calibration points include at least two points, wherein a first of the points is from detection of the first detection molecule bound to the first binding molecule only, present in the first concentration, and wherein a second of the points is from detection of the first detection molecule bound to the second binding molecule only, present in the second concentration, respectively.

2. The method of claim 1 wherein the binding molecules are recombinant antibodies, native antibodies, or peptide/protein biomarkers.

3. The method of claim 1 wherein the binding molecules are chimeric antibodies.

4. The method of claim 1 wherein the plurality of capturing agents is at least 5 different capturing agents.

5. The method of claim 1 wherein the capturing agents are allergen components, disease-related antigens, or antibodies specific for peptide/protein biomarkers.

6. The method of claim 1 wherein the first detection molecule is an anti-immunoglobulin conjugate or is an antibody specific for a peptide/protein biomarker.

7. The method of claim 1 wherein the solid phase is a microarray chip.

8. The method of claim 1 wherein the plurality of capturing agents is at least 50 different capturing agents.

9. The method of claim 1 wherein the capturing agents are antigenic components related to infectious disease or autoimmune disease.

10. The method of claim 1 wherein the first detection molecule is an antihuman IgE conjugate or an antihuman IgG conjugate.

11. The method of claim 1 wherein the calibration reagent comprises at least 15 different binding molecules.

12. The method of claim 1 wherein the calibration reagent comprises at least 5 different binding molecules.

13. The method of claim 12 wherein the calibration reagent comprises at least 5 different chimeric IgE antibodies, wherein each chimeric antibody has a capacity to bind specifically to an allergen component selected from the group consisting of Bet v 1, Der p 2, Ole e 1, Gal d 1, Art v 1, Fel d 1, Phl p 1, Amb a 1, Can f 1, Der p 1, Gal d 2, Can f 2, Can f 5, Phl p 5 and Pru p 3.

14. The method of claim 1, wherein the plurality of capturing agents immobilised on a solid phase, the first detection molecule and the calibration reagent are included in a multiplex assay system, and the system further comprises:
a reaction vessel, and
a reaction buffer medium.

15. The method of claim 14 wherein the plurality of analytes include (i) an IgE antibody, or (ii) an IgG antibody, or (iii) a peptide/protein biomarker for disease.

16. The method of claim 14 wherein the first detection molecule is (i) an anti-human IgE conjugate, (ii) an anti-human IgG conjugate, or (iii) an antibody specific for a peptide/protein biomarker.

17. The method of claim 14 wherein the binding molecules are recombinant antibodies, native antibodies, or peptide/protein biomarkers.

18. The method of claim 14 wherein the capturing agents are allergen components, or disease-related antigens, or antibodies specific for peptide/protein biomarkers.

19. The method of claim 14 wherein the calibration reagent comprises fifteen different mouse-human chimeric IgE antibodies, wherein each chimeric antibody has a capacity to bind specifically to an allergen component selected from the group consisting of Bet v 1, Der p 2, Ole e 1, Gal d 1, Art v 1, Fel d 1, Phl p 1, Amb a 1, Can f 1, Der p 1, Gal d 2, Can f 2, Can f 5, Phl p 5 and Pru p 3.

20. The method of claim 1 wherein the calibration reagent comprises at least two different antigenic biomarkers for cancer.

21. The method of claim 20 wherein the calibration reagent comprises at least two different antigenic biomarkers for prostate cancer.

22. The method of claim 20 wherein the calibration reagent comprises at least five different antigenic biomarkers for cancer.

23. The method of claim 21 wherein the capturing agents comprise at least two antibodies to which the at least two different antigenic biomarkers for prostate cancer respectively specifically bind.

24. A method for calibrating a multiplex assay operable to individually quantitatively detect a plurality of different analytes in a sample, comprising:
providing a solid phase with a plurality of capturing agents for the plurality of different analytes, respectively, immobilised on the solid phase,
adding a calibration reagent to the solid phase on which the plurality of capturing agents are immobilised, wherein the calibration reagent comprises at least four different binding molecules, wherein each binding molecule has a capacity to bind specifically to one of the plurality of capturing agents immobilised on the solid phase, wherein at least four of the binding molecules have different specificities, wherein of said at least four binding molecules, a first binding molecule is present in a first concentration, a second binding molecule is present in a second concentration, a third binding molecule is present in a third concentration, and a fourth binding molecule is present in a fourth concentration, and wherein the first, second, third and fourth concentrations differ from one another,
adding a first detection molecule to the solid phase, wherein each binding molecule has a capacity to bind to the first detection molecule,
detecting the bound first detection molecule, and
creating a single calibration curve comprising a plurality of calibration points, wherein the plurality of calibration points include at least four points, wherein a first of the points is from detection of the first detection molecule bound to the first binding molecule only, present in the first concentration, a second of the points is from detection of the first detection molecule bound to the second binding molecule only, present in the second concentration, a third of the points is from detection of the first detection molecule bound to the third binding molecule only, present in the third concentration, and a fourth of the points is from detection of the first detection molecule bound to the fourth binding molecule only, present in the fourth concentration, respectively.

\* \* \* \* \*

UNITED STATES PATENT AND TRADEMARK OFFICE
CERTIFICATE OF CORRECTION

| | |
|---|---|
| PATENT NO. | : 10,379,110 B2 |
| APPLICATION NO. | : 14/344894 |
| DATED | : August 13, 2019 |
| INVENTOR(S) | : Göran Elfverson et al. |

It is certified that error appears in the above-identified patent and that said Letters Patent is hereby corrected as shown below:

On the Title Page

Item (30), change "1150834" to --1150834-8--.

Signed and Sealed this
First Day of October, 2019

Andrei Iancu
*Director of the United States Patent and Trademark Office*